(12) United States Patent
Yeturu

(10) Patent No.: US 10,916,333 B1
(45) Date of Patent: Feb. 9, 2021

(54) ARTIFICIAL INTELLIGENCE SYSTEM FOR ENHANCING DATA SETS USED FOR TRAINING MACHINE LEARNING-BASED CLASSIFIERS

(71) Applicant: Amazon Technologies, Inc., Seattle, WA (US)

(72) Inventor: Kalidas Yeturu, Bangalore (IN)

(73) Assignee: Amazon Technologies, Inc., Seattle, WA (US)

( * ) Notice: Subject to any disclaimer, the term of this patent is extended or adjusted under 35 U.S.C. 154(b) by 880 days.

(21) Appl. No.: 15/633,424

(22) Filed: Jun. 26, 2017

(51) Int. Cl.
*G16B 40/00* (2019.01)
*G06F 17/15* (2006.01)
*G06F 17/18* (2006.01)
*G06K 9/62* (2006.01)

(52) U.S. Cl.
CPC ......... *G16B 40/00* (2019.02); *G06F 17/153* (2013.01); *G06F 17/18* (2013.01); *G06K 9/6269* (2013.01)

(58) Field of Classification Search
CPC ....... G16B 40/00; G06F 17/153; G06F 17/18; G06K 9/6269
See application file for complete search history.

(56) References Cited

U.S. PATENT DOCUMENTS

| | | | | |
|---|---|---|---|---|
| 6,801,657 B1* | 10/2004 | Cieplinski | ........... | G06F 16/5838 |
| | | | | 382/164 |
| 2005/0197980 A1* | 9/2005 | Dundar | ................ | G06K 9/6256 |
| | | | | 706/16 |
| 2006/0142976 A1* | 6/2006 | Bonanni | ............ | G05B 23/0281 |
| | | | | 702/189 |
| 2006/0245641 A1* | 11/2006 | Viola | .................... | G06F 40/295 |
| | | | | 382/155 |
| 2008/0159604 A1* | 7/2008 | Wang | ...................... | G06T 7/155 |
| | | | | 382/128 |
| 2011/0119209 A1* | 5/2011 | Kirshenbaum | .......... | G06N 5/02 |
| | | | | 706/12 |
| 2014/0324434 A1* | 10/2014 | Vozila | ..................... | G10L 15/18 |
| | | | | 704/257 |
| 2016/0055368 A1* | 2/2016 | Cao | ...................... | G06K 9/6206 |
| | | | | 382/195 |
| 2017/0293612 A1* | 10/2017 | Mistry | .............. | G06F 16/90344 |

OTHER PUBLICATIONS

Scikit Learn, "Feature transformation with ensembles of trees", Retrieved from URL: http://scikitlearn.org/stable/auto_examples/ensemble/plot_feature_transformation.html on Apr. 19, 2017, pp. 1-4.

(Continued)

*Primary Examiner* — Austin Hicks
(74) *Attorney, Agent, or Firm* — Robert C. Kowert; Kowert, Hood, Munyon, Rankin & Goetzel, P.C.

(57) ABSTRACT

A regression model is generated to map observation records of a first dimensionality to a second dimensionality. Using a set of transformed records obtained from the first regression model, a Gaussian mixture model of the distribution of observation records of the second dimensionality is trained. Using a Gaussian distribution obtained from the Gaussian mixture model, a recommended modification of a proposed training set of a classifier is obtained.

20 Claims, 11 Drawing Sheets

(56) References Cited

OTHER PUBLICATIONS

Wikipedia, "Multidimensional scaling", Retrieved from URL: https://en.wikipedia.org/wiki/Multidimensional_scaling on Jun. 10, 2017, pp. 1-7.
Burr Settles, "From Theories to Queries: Active Learning in Practice", JMLR: Workshop and Conference Proceeding 16, Workshop on Active Learning and Experimental Design, 2011, pp. 1-18.
Parisa Rashidi, et al., "Ask Me Better Questions: Active Learning Queries Based on Rule Induction", ACN, KDD 11, Aug. 21-24, 2011, pp. 1-9.
Gavin C. Cawley, "Baseline Methods for Active Learning", JMLR: Workshop and Conference Proceedings 16, Workshop on Active Learning and Experimental Design, 2011, pp. 47-57.
Steve Hanneke, "Theoretical Foundations of Active Learning", CMU-ML-09-106, Machine Learning Department, Carnegie-Mellon University, 2009, pp. 1-160.
Nicolo Cesa-Bianchi, et al., "Worst-Case Analysis of Selective Sampling for Linear Classification", Journal of Machine Learning Research 7, 2006, pp. 1205-1230.
Rui M. Castro, et al., "Minimax Bounds for Active Learning", IEEE Transactions on Information Theory, 5008, pp. 1-15.
Steve Hanneke, "A Bound on the Label Complexity of Agnostic Active Learning", Appearing in Proceeding of the 24th International Conference on Machine Learning, 2007, pp. 1-8.
Celine Vens, et al., "Random Forest Based Feature Induction", 2011 IEEE 11th International Conference in Data Mining, pp. 1-10.
Laurens Van Der Maaten, et al., "Visulaizing Data using t-SNE", Journal of Machine Learning Research 9, 2008, pp. 2579-2605.
Mario A.T. Figueiredo, et al., "Unsurpervised Learning of Finite Mixture Models", IEEE Transaction on Pattern Analysis and Machine Intelligence, vol. 24, No. 3, Mar. 2002, pp. 381-396.
David Arthur, et al., "k-means++: The Advantages of Careful Seeding", Proceedings of the eighteenth annual ACM-SIAM symposium on Discrete Algorithms, Society of Industrial and Applied Mathematics, 2007, pp. 1-9.
Markus Ringnér, "What is principal component analysis?", Nature Biotechnology, vol. 26, No. 2, Mar. 2008, pp. 303-304.
Masahi Sugiyama, et al., "Active Learning with Model Selection in Leaner Regression", Proceedings of the 2008 SIAM International Conference on Data Mining, Society for Industrial and Applied Mathematics, 2008, pp. 1-12.
Wikipedia, "t-distributed stochastic neighbor embedding", Retrieved from URL: https://en.wikipedia.org/wiki/Tdistributed_stochastic_neighbor_embedding on Apr. 18, 2017, pp. 1-3.
U.S. Appl. No. 15/719,402, filed Sep. 28, 2017, Mohammed Hidayath Ansari et al.

\* cited by examiner

ARTIFICIAL INTELLIGENCE SYSTEM FOR ENHANCING DATA SETS USED FOR TRAINING MACHINE LEARNING-BASED CLASSIFIERS

BACKGROUND

In recent years, as the costs of collecting and storing data has decreased, machine learning algorithms that analyze collected data sets for various types of predictions are being increasingly employed to increase the effectiveness of various services and applications. Large amounts of data with respect to user interactions with network-accessible applications (such as e-retail applications) may be collected, for example using logs generated at the applications, and used to enhance usability or customize user experiences with the applications. Similarly, data collected from numerous sensors may be analyzed to improve the functionality of various devices and algorithms, including algorithms for enhancing security, predicting failures, and so on.

Supervised learning is a common approach used for many types of machine learning problems. In supervised learning, a set of labeled input observations is used to train a model, and the trained model is then used to generate predicted labels for new unlabeled observations. For example, in a medical application, an individual patient's medical data record, comprising entries collected from various instruments, medical scanning/imaging devices and the like may be labeled to indicate whether the patient suffers from a particular illness or not. Large numbers of such labeled records may then be used as a training data set for a machine learning model, with the objective of subsequently using the trained model to predict the probability that a given patient (whose medical record was not part of the training data set and is thus unlabeled) suffers from the same illness.

In many cases the number of attributes or dimensions of a given input record which can be included in a training data set for a model may be quite large, and the relationships between the dimensions and the target or label attribute may be complex and nonlinear. The extent to which the training data is truly representative of the unlabeled data for which predictions eventually have to be made can have a significant impact on the quality of the predictions. Unfortunately, if the training set for a given machine learning model is not truly representative, it may take a very large amount of labeled data to train a model to make accurate predictions, and the effort required to label the data may be non-trivial.

Figure 1:
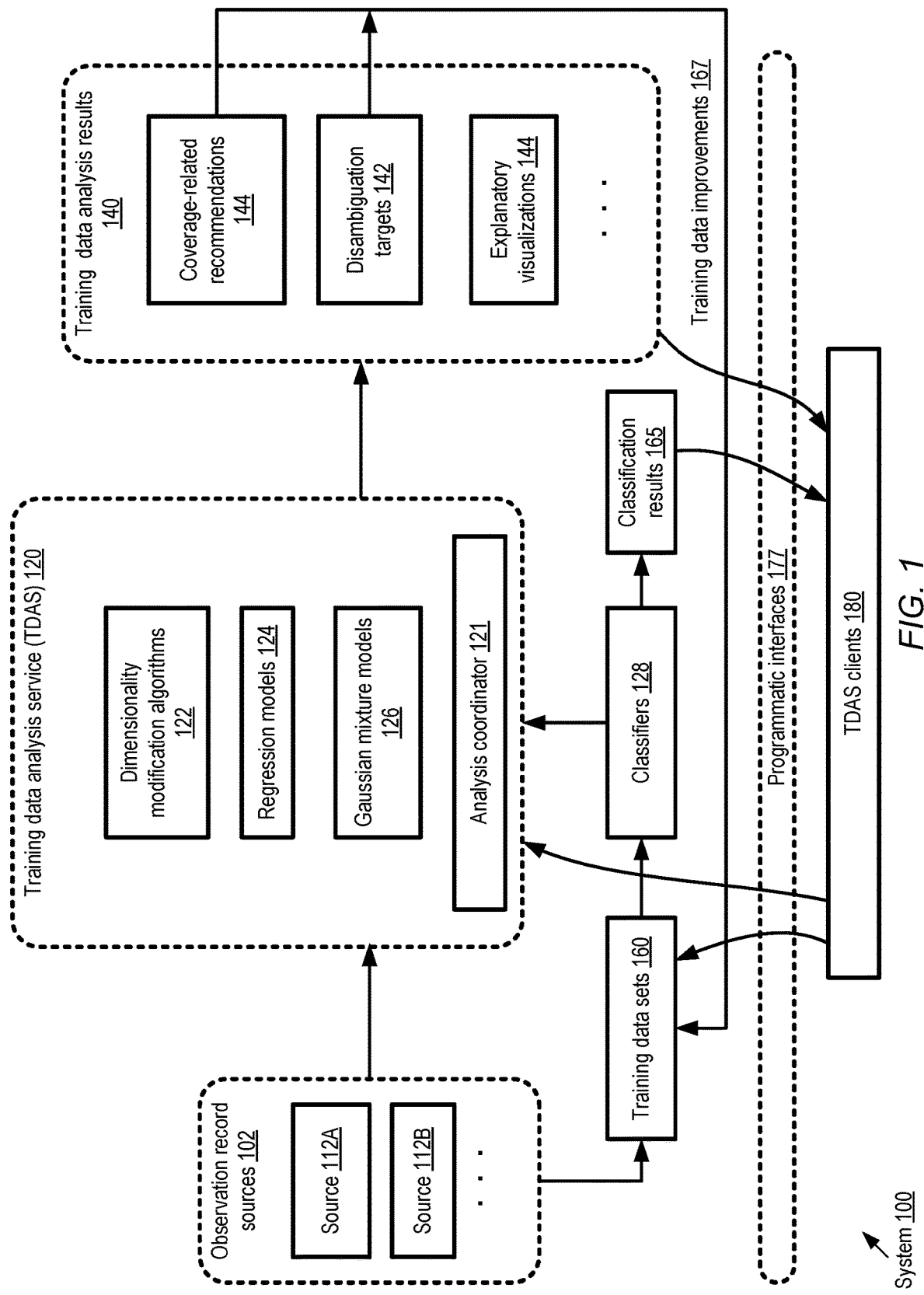
FIG. 1 illustrates an example system environment in which a data analysis service may be used to enhance the training of a classifier, according to at least some embodiments.

While embodiments are described herein by way of example for several embodiments and illustrative drawings, those skilled in the art will recognize that embodiments are not limited to the embodiments or drawings described. It should be understood, that the drawings and detailed description thereto are not intended to limit embodiments to the particular form disclosed, but on the contrary, the intention is to cover all modifications, equivalents and alternatives falling within the spirit and scope as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include," "including," and "includes" mean including, but not limited to. When used in the claims, the term "or" is used as an inclusive or and not as an exclusive or. For example, the phrase "at least one of x, y, or z" means any one of x, y, and z, as well as any combination thereof.

DETAILED DESCRIPTION

Various embodiments of methods and apparatus for analyzing and improving training data sets used for machine learning models are described. In at least some embodiments, one or more of the techniques described herein may be employed for "active learning", a methodology in which a large set of observations may be analyzed to identify a relatively small subset of observations which capture key aspects of the observations as a whole. After such a small subset is identified, in at least some embodiments a recommendation to generate (or disambiguate) labels for that small subset may be produced, or a recommendation to add the identified observations to a proposed training set may be produced. As a result of implementing the recommendations, in at least some embodiments the quality of the training data for one or more targeted models (such as classifiers) may be enhanced enough that a relatively small training data set may suffice to train the targeted models to generate high-quality results. In various embodiments, using relatively small training data sets may help reduce the effort and cost of labeling the data, and may also help reduce the resource usage and time needed for training the models.

According to some embodiments, a multi-stage methodology involving the use of a sequence of dimensionality modification algorithms, a non-linear regression model, and/or a Gaussian mixture model may be employed to analyze and improve training data using one or more computing devices of a training data analysis service or tool. In one embodiment, an indication of a data set comprising a plurality of observation records may be received. The data set may potentially be quite large, e.g., comprising millions or even billions of observation records in some cases. The observation records (which may also be referred to as data points or simply as points), some or all of which may potentially be included in a training set for one or more models, may individually comprise a feature set with a baseline dimensionality (i.e., a baseline number of attributes for which respective values are included in the observations). If the original or baseline attribute values are examined, e.g., in an attempt to cluster the observations for classification purposes, in at least some embodiments the boundaries between the clusters or classes may not be very clear, e.g., due to the non-linear relationships among the attributes.

Accordingly, a set of transformations may be applied to the observations in at least some embodiments in an attempt to more clearly separate groups or clusters of observations from one another. In a first transformation, in one embodiment the dimensionality of the observations may be increased, e.g., using a technique involving the generation of a random forest followed by one-hot encoding of the leaf nodes of the trees of the random forests. Other types of dimensionality expansion algorithms may be employed in different embodiments. The increase in dimensionality may, for example, help capture or clarify non-linear relationships among the dimensions/attributes, and may enable the separation of the observations into groups with less overlap than the baseline observations themselves. A value of a clustering quality metric (e.g., a metric of the extent of cluster separation) of the transformed data set with the higher dimensionality may exceed the value of the clustering quality metric of the baseline data set in at least some embodiments.

A dimensionality reduction algorithm may then be applied to the transformed data in various embodiments, e.g., to help visualize the clusters more easily. In this second transformation, in various embodiments the (high-dimensional) first transformed data set may be mapped to a second transformed data set with a lower number of dimensions, while preserving at least some of the spatial relationships between observations that were exhibited in the first transformed data set. Any of a variety of algorithms may be used for the reduction in dimensionality in different embodiments, such as a matrix factorization algorithm, a t-distributed stochastic neighbor embedding (TSNE) algorithm, a multi-dimensional scaling (MDS) algorithm or a Principal Component Analysis (PCA) algorithm. The TSNE technique may, for example, minimize the K-L divergence between points in a high dimensional space of the first transformed data set and a two-dimensional second transformed data set, thereby retaining "neighborhood" relationships of the higher dimensionality space across the mapping to the two-dimensional space. In some embodiments, the second transformation may result in data with more than two dimensions.

The lower-dimensional transformed data set may be considered a multivariate output vector relative to the baseline or original data set (the data set prior to the dimensionality transformations), and a non-linear regression model may be trained in at least some embodiment for mapping the baseline input observations to a low-dimension transformed data set. The non-linear regression model may employ a random forest based algorithm in some embodiments; other regression algorithms may be employed in different embodiments. Once trained, the non-linear regression model may eliminate the need perform multiple dimensionality transformation for new observations in at least some embodiments; that is, the non-linear regression model may be used directly to map observation records (with the baseline or original dimensionality) to transformed records with a small number of dimensions (e.g., two dimensions) in such embodiments.

For a given set of observations with the feature set of the baseline or original data, a point cloud representation may be produced using Gaussian mixture models in at least some embodiments. The non-linear regression model may be used to obtain the low-dimensional transformations from the observations, and a Gaussian mixture model may be trained using the low-dimensional transformations in various embodiments. A Gaussian mixture model may represent the distributions of observation records of the low-dimensionality as a plurality of Gaussian distributions, each of which may for example be visualized as respective ellipsoids. The means and standard deviations of the individual Gaussian distributions may be used to identify a number of points or observations for which label disambiguation may be advisable in at least some embodiments to help improve the quality of the training data, as described below in further detail. The recommended number of such observations for which labels should be verified or disambiguated may be referred to as a "disambiguation count" in some embodiments. The disambiguation count (and/or the specific points/observations for which label disambiguation is recommended) may be generated as an output of the training data analysis service or tool in various embodiments. The disambiguation count and/or the corresponding observations may be provided to a client in some embodiments via a programmatic interface, or a representation thereof may be stored in a repository.

In one embodiment, the respective output or results of the Gaussian mixture model with respect to a proposed training set and a test set for a classifier may be compared, e.g., to determine whether modifications such as adding a set of points to the proposed training set may improve the coverage provided by the training data relative to the test data. In some embodiments, an iterative optimization algorithm may be employed as more observations are identified using the comparison of the Gaussian model results. In such an algorithm, an axis corresponding to an ellipsoid representation of a Gaussian distribution obtained from the model may be partitioned, based at least in part on a variation-related metric of the Gaussian distribution. For example, the axis may be subdivided into segments corresponding to a distance of one standard deviation from the centroid, two standard deviations from the centroid, and so on. In successive iterations, a result set from a model targeted for improvement (such as a classifier) may be obtained using training sets modified by adding observations within successively larger sub-segments of the axis may be obtained, until a desired quality of model output is attained. For example, in one iteration, observations mapped to the distance corresponding to one standard deviation from the centroid may be added to the training data set, in a subsequent iteration observations mapped to the distance corresponding to two standard deviations from the centroid may be added to the training data set, and so on. In at least one embodiment, at least some of the recommendations generated by the analysis of the kind described above (such as addition of observations to the training data set to improve coverage relative to a test set) may be implemented in an automated manner to improve the training data, e.g., without requiring further actions to be taken by clients of the service. Similar computations bases on partitioning the axis may be used to identify a set of observations whose labels are to be disambiguated in at least some embodiments.

In various embodiments, the training data analysis service or tool may provide visualizations of data produced at various stages of the analysis. In one embodiment, for example, a client of the data analysis service (such as a data scientist) may programmatically indicate the particular analysis phase whose output or input is to be displayed visually. In one implementation, for example, a flow chart may be prepared and displayed indicating the stages of the analysis, and a client may click on various elements of the flow chart to indicate the particular stage for which a visualization is desired. The client may, for example, wish to view the distribution of data points after the first expansion of dimensionality, after the dimensionality contraction phase, after the Gaussian mixture model has been trained, and so on. In various embodiments one or more programmatic interfaces may be implemented by the training data analysis service for client interactions, such as a set of application programming interfaces or APIs, a web-based console, command-line tools, and/or graphical user interfaces. Requests to perform training data analysis for one or more targeted models (such as classifiers) may be submitted by clients via such interfaces in some embodiments, leading to the execution of a multi-stage technique of the kind described above. In various embodiments, visualization requests may be submitted via the programmatic interfaces, indicating for example the particular data set(s) and the analysis phase whose output or input is to be visualized, and so on. For example, one request may indicate that the ellipsoid representations of Gaussian distributions for a proposed training data set and/or a test or post-training data set are to be displayed. In response to a visualization request, the training data analysis service may prepare a data set comprising values of one or more dimensions of output (or input) records generated by (or for) the analysis phase for visual presentation in various embodiments. The data set and a directive to display the data contained in the data set may be transmitted to a destination device comprising a display in some embodiments.

In at least one embodiment, the training data analysis may be performed using resources of a provider network or public cloud environment. In at least one embodiment, a standalone tool implemented at one or more computing devices, which performs training data analysis using a combination of transformations, models and other algorithms similar to those described above without using provider network resources may be used—that is, the use of a provider network is not a requirement for the techniques described herein.

Example System Environment

FIG. 1 illustrates an example system environment in which a data analysis service may be used to enhance the training of a classifier, according to at least some embodiments. As shown, system 100 may comprise resources and artifacts of a training data analysis service 120, including one or more analysis coordinators 121 responsible for implementing a multi-stage training data analysis methodology in some embodiments. The analysis coordinators may comprise one or more hardware and/or software components or modules. For example, one or more computing devices comprising processors and memory containing executable instructions may be used for an analysis coordinator 121 in some embodiments.

The training data analysis service 120 may be used to improve or increase the training efficiency of one or more machine learning models in various embodiments. In FIG. 1, one or more classifiers 128 represent an example of the kinds of models whose training may be enhanced using the training data analysis service; in other embodiments, training for other types of machine learning models may be improved using similar techniques to those described herein with respect to classifiers 128. In general, training data sets 160 may be constructed for a classifier 128 using observation records generated at one or more sources 102, such as source 112A or 112B. Examples of such sources may include application logs, sensors of various kinds, administrative or database records, and so on, depending on the application or problem domain for which the classifier 128 is to be trained. In at least some embodiments, large volumes of unlabeled observation records may be available for inclusion in the training data sets, and individual observation records may comprise values for numerous attributes or dimensions. After a classifier has been trained using one or more training data sets 160 (which may have been enhanced or improved using the recommendations and/or visualizations which form the training data analysis results 140), the classifier may be deployed for production or post-training use in the depicted embodiment. Classification results 165 (such as respective labels, or a set of classification scores corresponding to several feasible labels) may be generated for previously-unseen observations using the classifiers 128 in the depicted embodiment.

In at least some embodiments, the distribution of the values of the attributes of the observation records produced by source 102 may be such that it is hard to discern class boundaries among the observations. Observation records may comprise large numbers of attributes (representing a high baseline dimensionality), some of which may have non-linear relationships to other attributes, resulting in it being difficult to group the unmodified or baseline observations into clearly separated clusters or classes. In order to help clarify the impact of the non-linear relationships and help identify distinct classes, in at least some embodiments a process of successive dimensionality modifications may be applied to a potentially large subset of the baseline or original data. In one embodiment, for example, a random forest may be constructed using the observations, and then a one-hot encoding technique may be applied (e.g., to encode representations of the observations corresponding to leaf nodes of the random forest's trees) to expand the dimensionality of the baseline data, resulting in a first intermediate set of transformed records. In the higher dimensional space, it may be the case that the clusters become more distinct, as the impact of non-linear relationships may be made clearer. A second dimensionality transformation may be applied to help visualize the data, e.g., by reducing the dimensionality to a small number (such as two dimensions or three dimensions) while retaining proximity relationships which were present in the higher dimensional data. Dimensionality modification algorithms 122 may comprise a variety of dimensionality contraction/reduction techniques in different embodiments, such as TSNE, PCA, matrix factorization and/or MDS, as well as dimensionality expansion algorithms such as those based on random forests and one-hot encoding.

From some selected subset of the original observation data, a transformed set of low-dimensional records (such as two-dimensional or three-dimensional records) may be created using the dimensionality modification algorithms as discussed above in the depicted embodiment. A regression model 124 may be trained using the observations and their low-dimensional mappings in various embodiments, in effect generating a tool which can be used to obtain low-dimensional mappings for any observations which have the same feature set as the original observations. Using the low-dimensional results obtained from the trained regression model for another subset of the original or baseline observation data, a Gaussian mixture model 126 may be trained by the analysis coordinator 121 to represent the distributions of different observation classes or point clouds in at least some embodiments. Individual Gaussian distributions for the different classes may be representable as ellipsoids in at least some embodiments.

Using a combination of dimensionality transformations, regression models and Gaussian mixture models, an analysis coordinator 121 may be able to generate several types of recommendations regarding training data sets in various embodiments. For example, from among a potentially large set of ambiguously-labeled records of a proposed training data set for a classifier 128, a small number of disambiguation target records 142 (obtained by using a version of the classifier 128) may be identified for label verification in some embodiments. For example, in one binary classification scenario, it may be the case that several thousand observations have a classification score in the range 0.48-0.52, where 0.5 is the boundary score between the two classes being considered. Because of the proximity of the score to the boundary, those several thousand records may be considered potential candidates for disambiguation (e.g., using subject matter experts and/or an automated tool for disambiguating). Using the means and standard deviations of the Gaussians, a small subset (e.g., tens or hundreds) of the ambiguous observations may be identified as actual targets for disambiguation in some embodiments; such a small subset may be referred to as an "active" set in some embodiments.

Similarly, by comparing the Gaussian distributions of various classes in a proposed training set with the distributions of various classes in a test (post-training) data set, coverage-related recommendations 144 may be generated in at least one embodiment. For example, if the comparison indicates that for at least one class or cluster present in the test data, there are no corresponding observations (or insufficient corresponding observations) in the training data, some number of appropriately-selected observations similar to those of the test data should be added to the proposed training data. The recommendations generated by the analysis may be used to implement training data improvements 167 in various embodiments, e.g., in an automated manner—for example, observations with desired characteristics may be added to the proposed training set, and/or some observation labels may be verified using active learning techniques. The improved training data may be used to re-train the classifier 128, and the quality of the classification results 165 may be improved as a result of the modifications of the training data. The content of the recommendations, such as the disambiguation count (the number of observations to be disambiguated) or the to-be-disambiguated observations themselves may be stored and/or provided/transmitted to a destination such as a client 180 in some embodiments.

In at least some embodiments, explanatory visualizations 144 may be provided with respect to various phases of the analysis and accompanying data transformations. For example, as discussed below in further detail, a client may submit visualization queries or requests via programmatic interfaces 177, view the distributions of the original data as well as intermediate data at different stages of the analysis, and/or explore the impact of changing various meta-parameters (such as random forest tree counts and minimum depths). The visualizations 144 may help clients 180 in several ways in the depicted embodiment—e.g., to gain a better intuitive understanding of the data, to enable sanity checks with regard to the analysis, to explore the meta-parameter space, and so on. It is noted that as the original observations are transformed during the analysis, mappings between the transformed versions of the records and the original observations may be retained in at least some embodiments, so that for example it is possible to identify the original observation to which a transformed record corresponds. Such mappings may be used, for example, to move back and forth in a visualization interface between a transformed data point and its corresponding original observation. A variety of programmatic interfaces 177 may be implemented in different embodiments, such as a set of application programming interfaces (APIs), a web-based console, command-line tools and/or graphical user interfaces. The techniques described may be applied to improve models other than classifiers in at least some embodiments.

Multi-Stage Technique for Training Data Analysis

Figure 2:
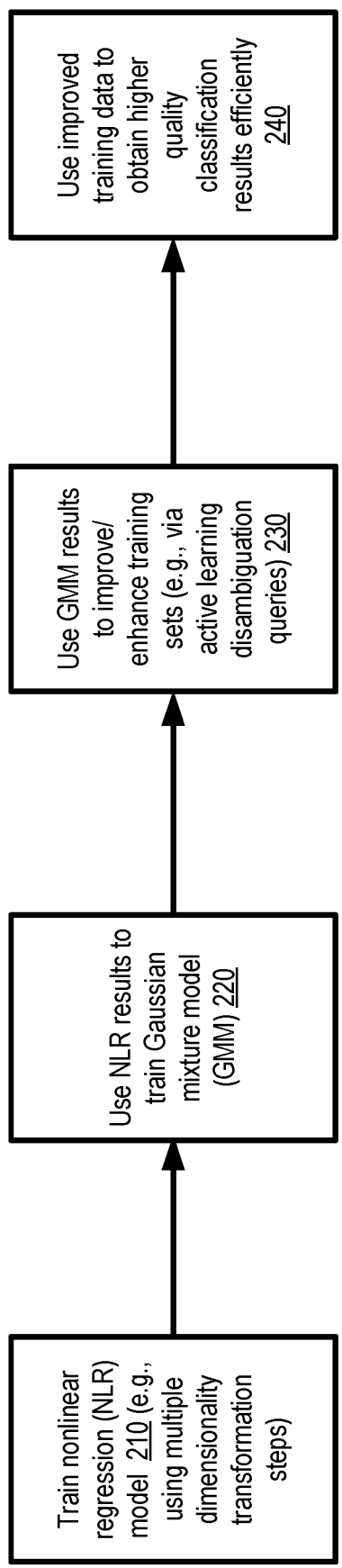
FIG. 2 illustrates a high level overview of an example multi-stage technique employing non-linear regression models and Gaussian mixture models for training data set analysis, according to at least some embodiments.

FIG. 2 illustrates a high level overview of an example multi-stage technique employing non-linear regression models and Gaussian mixture models for training data set analysis, according to at least some embodiments. In the first stage, a non-linear regression (NLR) model 210 may be generated from a set of observation records, e.g., using multiple dimensionality transformation steps/algorithms as discussed earlier. The output of the NLR may comprise a low-dimensional transform of input observations in various embodiments.

In the second stage, results from the regression model 210 may be used to train a Gaussian mixture model (GMM) 220 comprising respective Gaussian distributions corresponding to various classes or clusters seen in the low-dimensional transforms produced by the regression model. If, for example, the regression model produces two-dimensional transformed records as output, the Gaussian distributions may be represented by ellipsoids in a visualization interface, making it easier to compare the distributions of records of proposed training sets and post-training test data.

After the GMM has been trained, it may be utilized to improve or enhance training sets in the depicted embodiment, e.g., via active learning disambiguation queries as indicated in element 230 and/or by improving the coverage of training sets relative to test data. The improved training data may be used to obtain higher-quality classification results efficiently (element 240), e.g., without having to use extremely large training sets and the corresponding computational, memory and storage resources in various embodiments. In at least some embodiments, starting with a large set of observation records (e.g., millions or billions of observations), respective subsets of the observation data may be extracted and utilized at the different workflow stages shown in FIG. 2. In various embodiments, as a given observation record is transformed during the workflow, a pointer to the original (untransformed) version and/or respective pointers to other transformed versions of the record may be maintained, making it possible to correlate the transformed versions with one another and with the original version. Such correlation information may be provided via visualization tools to clients in some embodiments—e.g., a client may be able to trace the same observation record visually across the different transformation/mapping steps (in the forward or backward direction) if desired.

As indicated in FIG. 2, a number of different machine learning models may be used in the process of analyzing and improving training data. In various embodiments, implementations of each of the models may, for example, include memory for storing input values and parameters and computer-executable instructions for an initial set of computations on the input values. In some embodiments, intermediary layers of a model may include memory storing computer-executable instructions and/or data for manipulating the results of the initial computations and determining values to be transmitted to an output layer. The output layer may in turn include memory and/or computer-executable instructions for generating and/or storing output values. Any of a number of types of data structures may be used for storing data and/or implementing the algorithm logic, e.g., including various tree-based structures as well as data structures optimized for storing matrices, vectors, arrays, hash tables and the like.

Non-Linear Regression Model

Figure 3:
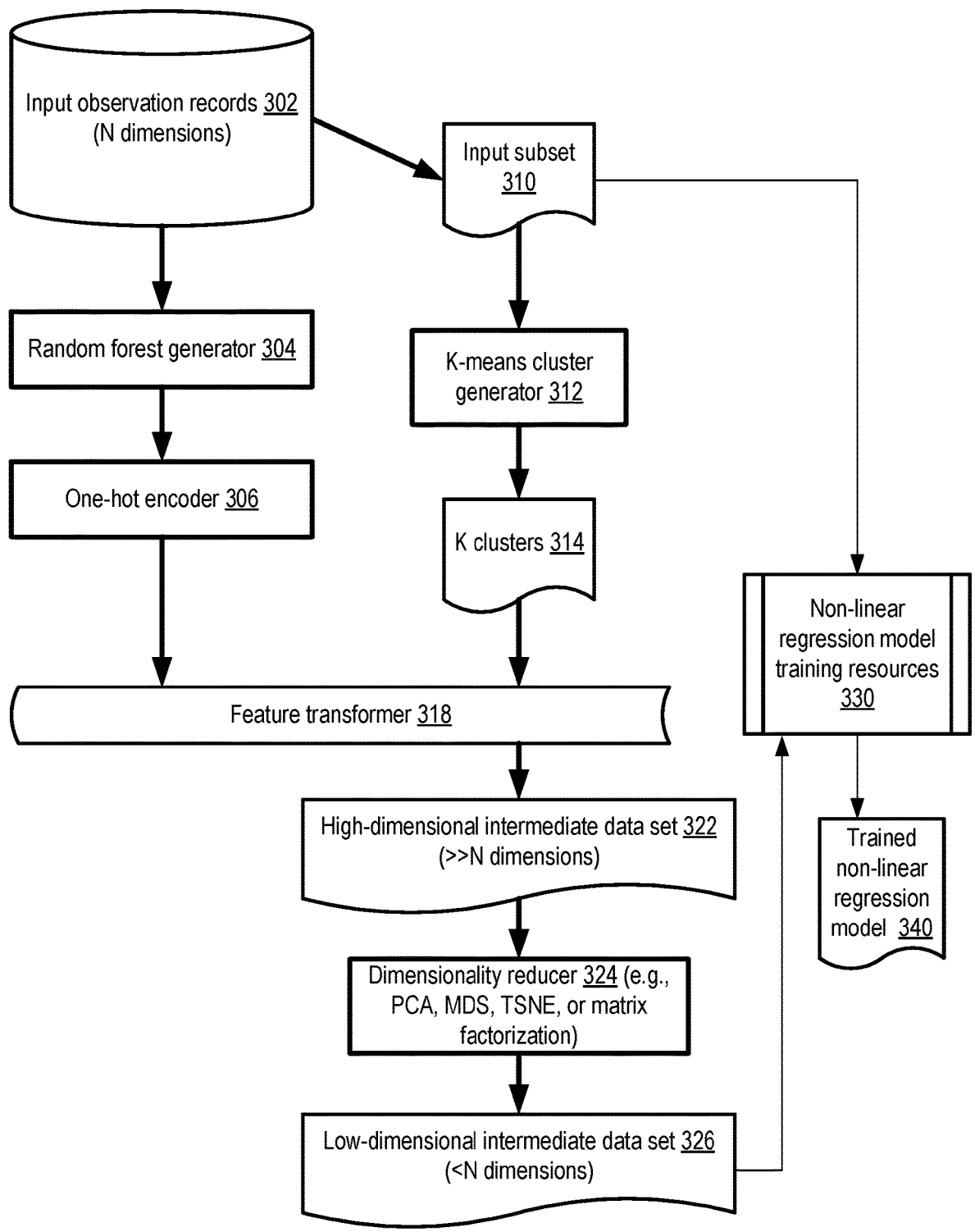
FIG. 3 illustrates aspects of example operations which may be performed to train a non-linear regression model which maps input data records to an intermediate set of records of a desired low dimensionality, according to at least some embodiments.

FIG. 3 illustrates aspects of example operations which may be performed to train a non-linear regression model which maps input data records to an intermediate set of records of a desired low dimensionality, according to at least some embodiments. In the depicted embodiment, individual ones of input observation records 302 may comprise values for N attributes or dimensions, some of which may have non-linear relationships with other dimensions of the records. As such, N may represent the baseline or original dimensionality of the data in the depicted embodiment. A selected number of observation records 302 of the baseline dimensionality may be provided as input to a random forest generator 304 in various embodiments. The trees produced by the random forest generator 304, in which leaf nodes correspond to individual observations, may be provided as input to a one-hot encoder 306, resulting in effect in an increase in the number of dimensions of the data records. The combination of the random forest and one-hot encoding techniques may represent a feature transformer 318 in the depicted embodiment.

A subset 310 of the input observations may be divided into clusters using a K-means cluster generator 312 in the depicted embodiment. The observations corresponding to the K clusters 314 may be fed as input to the feature transformer 318, producing a high-dimensional intermediate data set 322 which may have a much higher number of dimensions (>>N) than the original input data records in the depicted embodiment. The expansion in dimensionality may help clarify or represent the non-linear relationships in the original data in at least some embodiments. Next, a dimensionality reducer 324 (such as an implementation of matrix factorization, PCA, MDS or TSNE) may be applied to the high-dimensional intermediate data set 322 to produce a low-dimensional intermediate data set 326. In some embodiments, for example, the number of dimensions of the data set 326 may be set to two. As such, the individual records of data set 326 may be considered multivariate output vectors corresponding to the records of input subset 310, and may be used to train a non-linear regression model using resources 330 in the depicted embodiment. The trained non-linear regression model 340 produced may be capable of generating a low-dimensional mapping from observation records with the original or baseline dimensionality N in the depicted embodiment. The records of data set 322 (with increased dimensionality relative to the original input data) and 326 (with decreased dimensionality relative to the records of data set 322) may be referred to as intermediary records or intermediate records in at least some embodiments.

In some embodiments, random forest generator 304, one-hot encoder 306, K-means cluster generator 312, dimensionality reducer 324, and/or non-linear regression model training resources 330 may comprise respective computing devices. In other embodiments, at least some of the components shown in FIG. 3 may be implemented using a shared set of computing devices.

Gaussian Mixture Model

Figure 4:
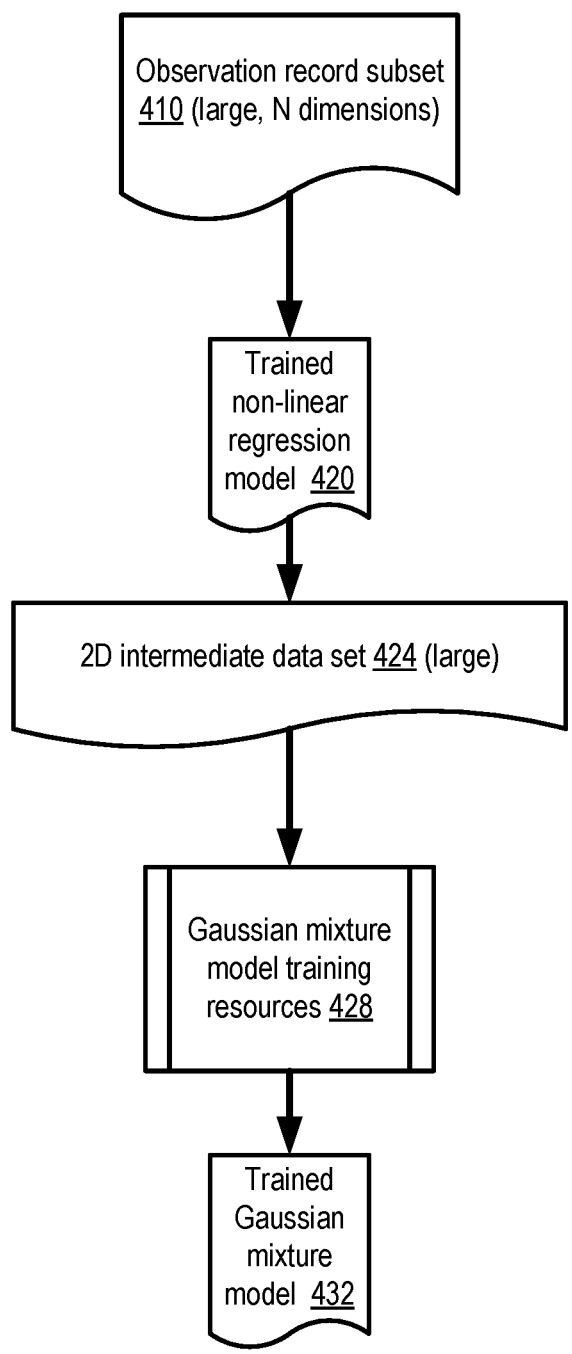
FIG. 4 illustrates aspects of example operations which may be performed to train a Gaussian mixture model to represent distributions of intermediate data produced as output by a non-linear regression model, according to at least some embodiments.

FIG. 4 illustrates aspects of example operations which may be performed to train a Gaussian mixture model to represent distributions of intermediate data produced as output by a non-linear regression model, according to at least some embodiments. As shown, an observation record subset 410 may be identified to train the Gaussian mixture model in the depicted embodiment. The subset 410 may include records with the baseline N dimensions, and may comprise a selected large number of records.

A trained non-linear regression model 420 may consume the observation record subset 410 as input and produce a two-dimensional intermediate data set 424 as output, e.g., with the output comprising the same number of records as the input. The two-dimensional data set 424 may be used as input at training resources 428 to generate a Gaussian mixture model, with individual ones of the Gaussian distributions of the mixture representing respective classes or clusters of the data. The trained Gaussian mixture model 432 may then be used to generate recommendations for improving the training set of a classifier or other model as discussed in further detail below. In some embodiments, the non-linear regression model 420 may be run at a separate computing device than the devices used for training the Gaussian mixture model. In other embodiments, shared resources may be used for training and executing the non-linear regression model as are used for the Gaussian mixture models. The number of Gaussian distributions to include in the mixture model may represent a meta-parameter of the training data analysis in at least some embodiments. In one embodiment, a metric such as Mahalanobi's distance may be used to determine a threshold number of data records corresponding to each of the Gaussian distributions which should be included in a training set.

Identifying Records for Label Disambiguation

Figure 5:
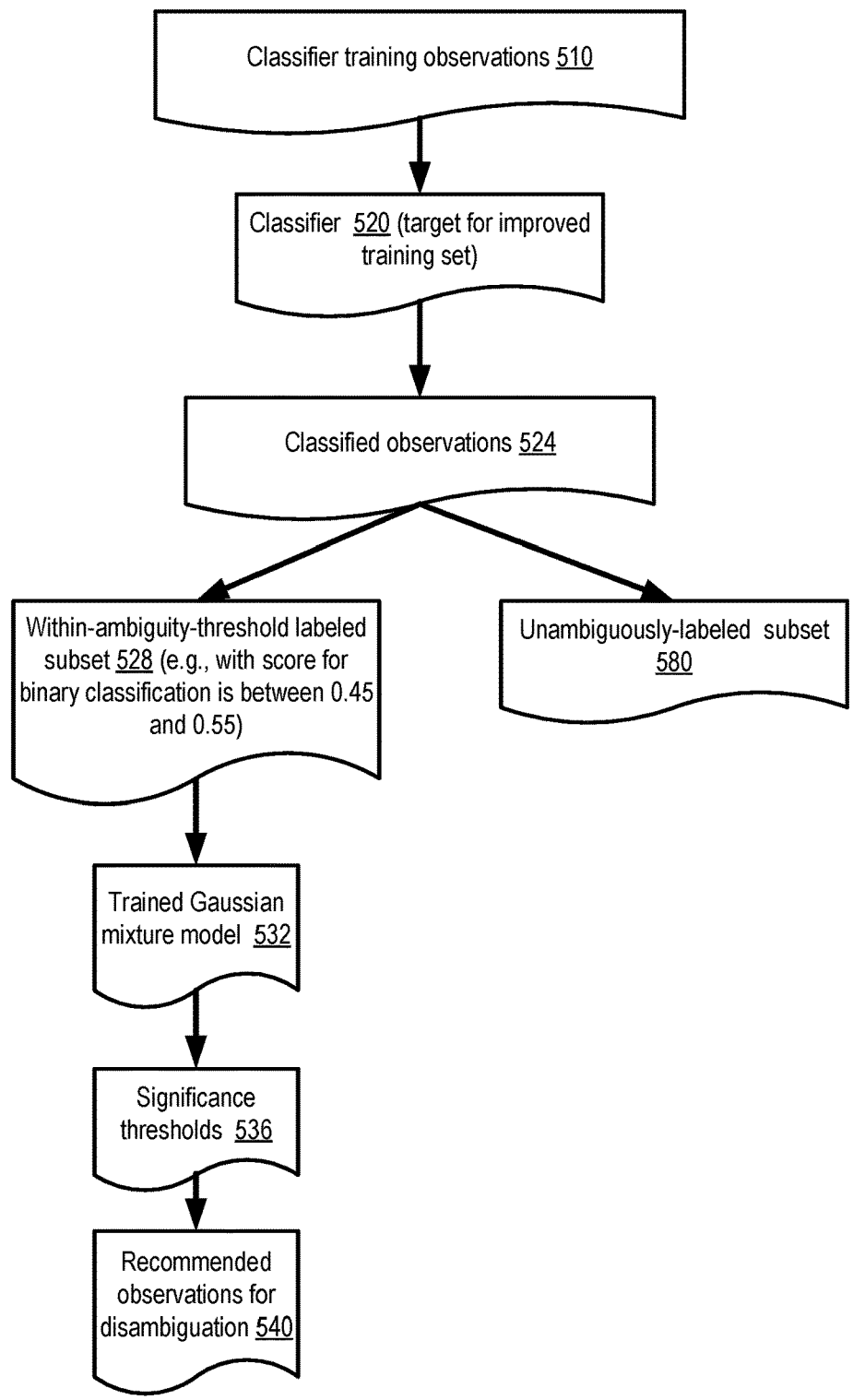
FIG. 5 illustrates aspects of example operations which may be performed to identify, using a Gaussian mixture model, data records which are recommended for label disambiguation, according to at least some embodiments.

FIG. 5 illustrates aspects of example operations which may be performed to identify, using a Gaussian mixture model, data records which are recommended for label disambiguation, according to at least some embodiments. In the depicted embodiment, a binary classifier is presented as an example model for which training data is analyzed for possible improvements. A selected set of training observations 510 may initially be used to train the classifier 520 in the depicted embodiment. For each classified observation 524, a respective classification score may be determined by the classifier 520, such as a real number in the range 0.0 to 1.0, with 0.5 as the boundary between the classes The scores originally assigned by the classifier 520 to a subset of the observations may lie within an ambiguity threshold in the depicted embodiment. For example, observations whose scores are set to values between 0.45 and 0.55 may be considered members of within-ambiguity-threshold labeled subset 528 in one embodiment, while observations whose labels are less than 0.45 or greater than 0.55 may be considered members of the unambiguously-labeled subset 580. In some embodiments, the member records of the ambiguous subset 528 may be identified automatically. For example, using one or more classification score thresholds (which may themselves be adapted or learned over time in some embodiments), a candidate set of observation records of the proposed training set to be evaluated for disambiguation may be identified, and provided as input to the Gaussian mixture model.

The ambiguous data may be processed using the trained Gaussian mixture model 532 in the depicted embodiment. Significance thresholds 536, e.g., computed using the means and standard deviations (or other variation-related metrics) of the Gaussian distributions, may be used to identify a small subset of observations 540 for label disambiguation in at least some embodiments. For example, some number of observations which lie within one standard deviation of the mean may be selected for disambiguation, and the classifier may be retrained with modified training data in which the labels of the selected observations are verified or disambiguated. The disambiguation count (the number of observations to be disambiguated) or the to-be-disambiguated observations themselves may be stored and/or provided/transmitted to a destination such as a client device in some embodiments. If the classifier's results do not meet a quality threshold, a subsequent iteration of training may be attempted in which the labels of more observations (e.g., within two standard deviations of the means of the Gaussians) are verified, and so on, until the quality of classification results meets a threshold.

Figure 6:
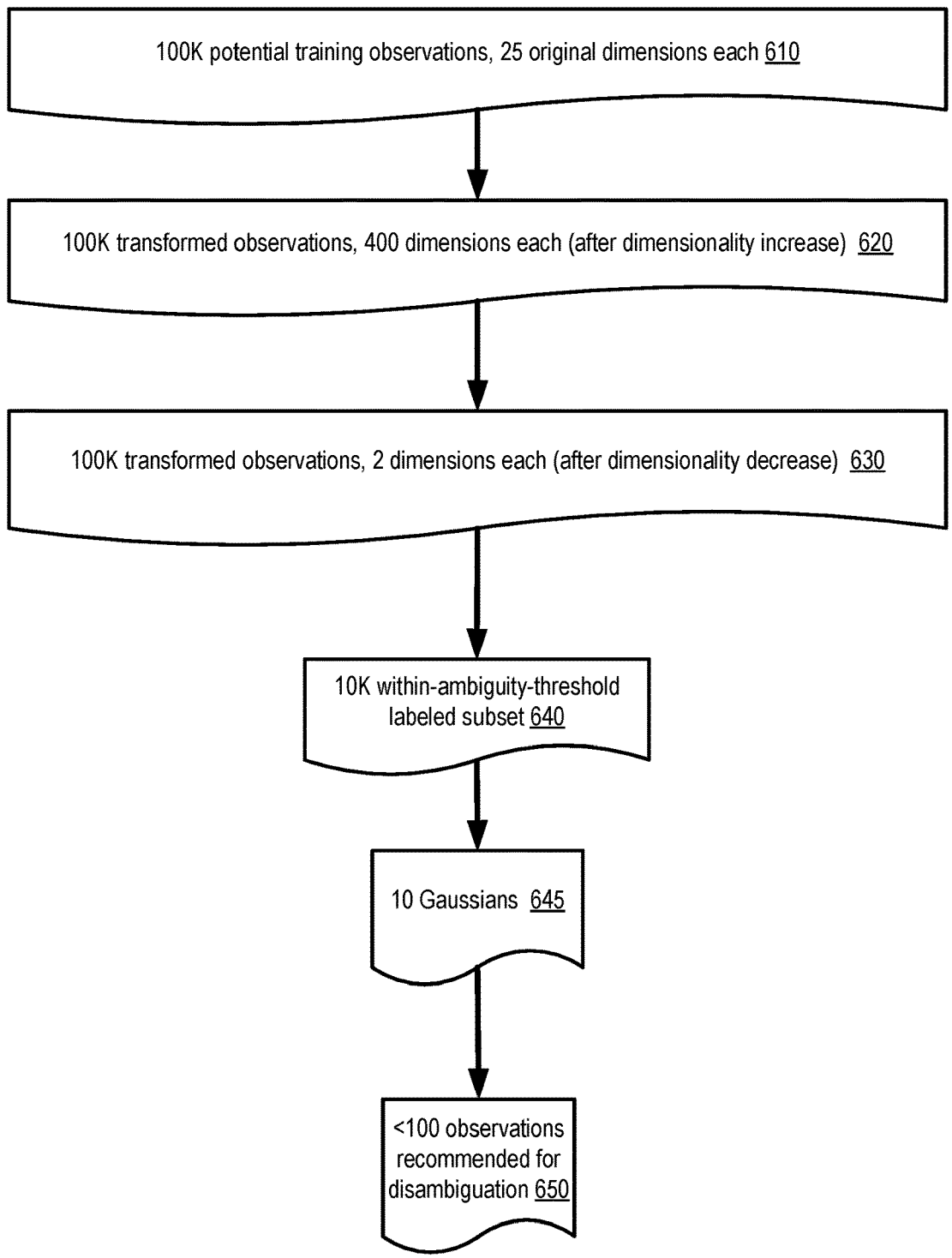
FIG. 6 illustrates an example scenario in which a small number of data records may be identified, using the Gaussian mixture model, as disambiguation candidates from a much larger set of ambiguous records, according to at least some embodiments.

Using the Gaussian mixture model, a significant reduction in the number of records which have to be disambiguated may be achieved, relative to the full set of ambiguously-labeled records in at least some embodiments. FIG. 6 illustrates an example scenario in which a small number of data records may be identified, using the Gaussian mixture model, as disambiguation candidates from a much larger set of ambiguous records, according to at least some embodiments. In the depicted example scenario, 100,000 (100K) original or baseline (untransformed) observation records may be potentially available for training, as indicated in element 610. By way of example, each of the observations may comprise respective values for 25 original dimensions or attributes.

The dimensionality of the data may be increased, e.g., using the random forest and one-hot encoding approach discussed earlier, resulting in 100K transformed observations with (by way of example) 400 dimensions each as indicated in element 620. Using a dimensionality reduction algorithm (such as matrix factorization, TSNE, PCA or MDS), a second transformed 100K-record data set 630 with (for example) just two dimensions each may be produced in the depicted example scenario.

Within the two-dimensional data, assume that 10,000 records lie within a selected ambiguity threshold with respect to a classifier in the depicted example scenario, as indicated in element 640. Assume further that a mixture of 10. Gaussian distributions 645 is used, each of which is used to select less than 10 points for label disambiguation. As indicated in element 650, out of the total of 10,000 ambiguously-labeled records, less than 1% (100) of the observations may be identified for disambiguation, representing a very low overhead for improving the training data.

Coverage Analysis of Proposed Training Data

Figure 7:
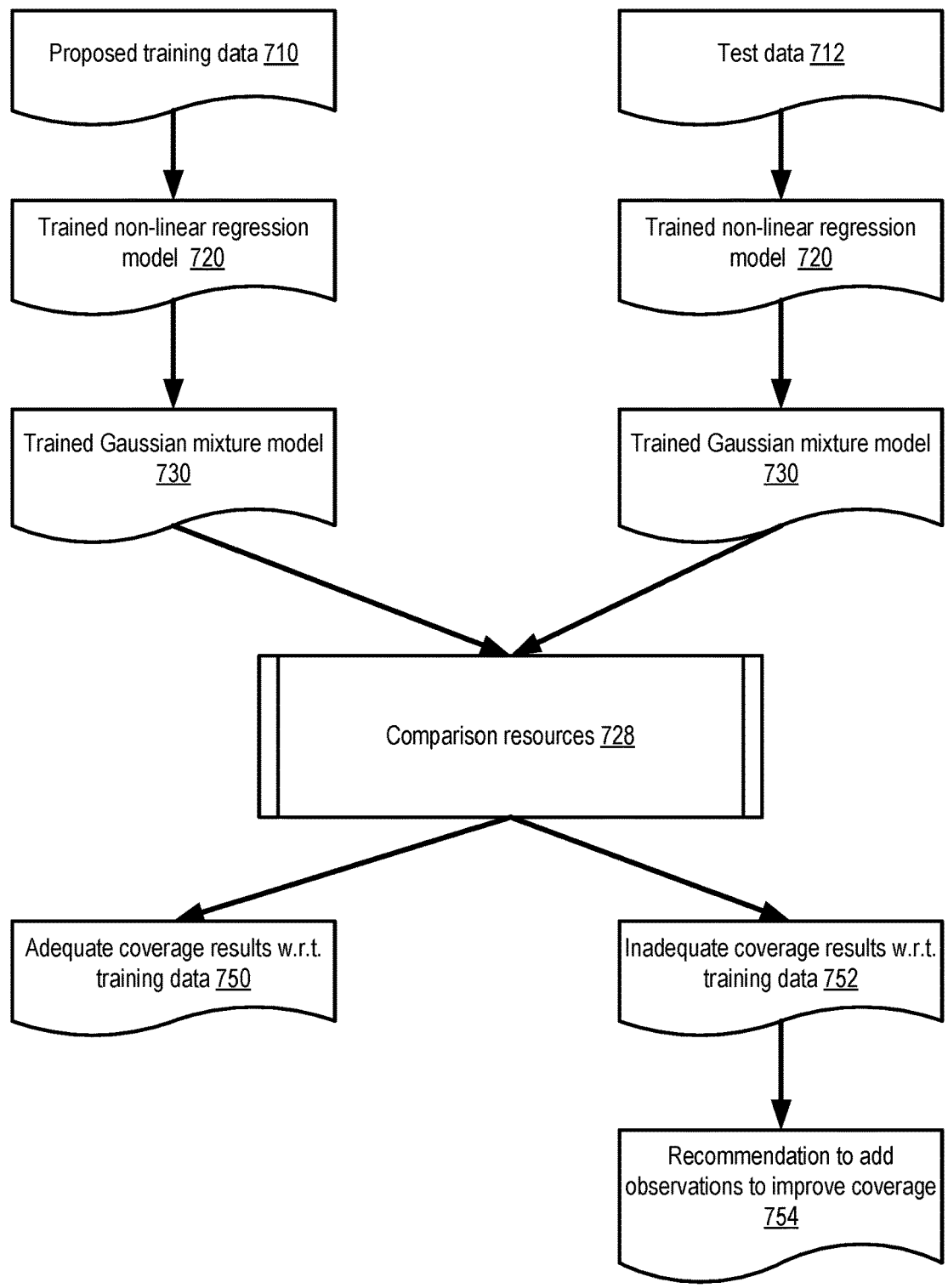
FIG. 7 illustrates aspects of example operations which may be performed to determine, using a Gaussian mixture model, that some characteristics of a test data set may not be adequately covered by a proposed training data set, according to at least some embodiments.

FIG. 7 illustrates aspects of example operations which may be performed to determine, using a Gaussian mixture model, that some characteristics of a test data set may not be adequately covered by a proposed training data set, according to at least some embodiments. In the depicted embodiment, a proposed training data set 710 and a test data set 712 may each be provided separately as input a trained non-linear regression model 720. The respective outputs produced by the regression model 720 for the two data sets may in turn be provided as input to the trained Gaussian mixture model 730. The output produced by the Gaussian mixture models for the proposed training data and the post-training or test data may be compared using an algorithm 728.

The results of the comparison algorithm may indicate either that coverage of one or more observation clusters or classes identified in the test data using the Gaussian mixture model is adequate (as indicated in element 750) or inadequate (as indicated in element 752) in the depicted embodiment. Adequate coverage 750 may imply that with respect to each of the clusters or classes, there are sufficient observations present in the proposed training data set, where the sufficiency of the observations for a given class may be indicated by a selected metric associated with the Gaussian distribution of the class. For example, in one embodiment, for each class, a minimum of N observations within P standard deviations of the mean of a given Gaussian distribution may have to be present in the proposed training set for the coverage to be considered sufficient, where N and P are meta-parameters of the model. Inadequate coverage 752 may indicate that for at least one class, more observations representative of that class should be added to the proposed training set. As such, in the scenario in which the coverage is found to be inadequate, the training data analysis service may generate a recommendation 754 to add observations with specific characteristics to improve the coverage in at least some embodiments. In one embodiment, the training data analysis service may be provided a larger pool of observations from which the proposed training set has been selected, and the service may automatically select some observations from that larger pool for inclusion in the training set based on the results of the comparison algorithm 728.

Visualization-Related Interactions

As described above, multiple phases of analysis, using various transforms, models and algorithms, may be employed to determine whether any modifications should be made to training data for a targeted model in various embodiments. Several or all of the phases may require a set of decisions to be made regarding meta-parameters—for example, the number of trees to be generated for a random forest used in the dimensionality expansion phase may have to be selected, the size of a test data set to be used for comparisons with a proposed training data set may have to be selected, and so on. Visualizing the results of processing at various stages of the analysis may be useful in understanding the distribution of the data classes or clusters, and/or in selecting meta-parameter values in various embodiments.

Figure 8:
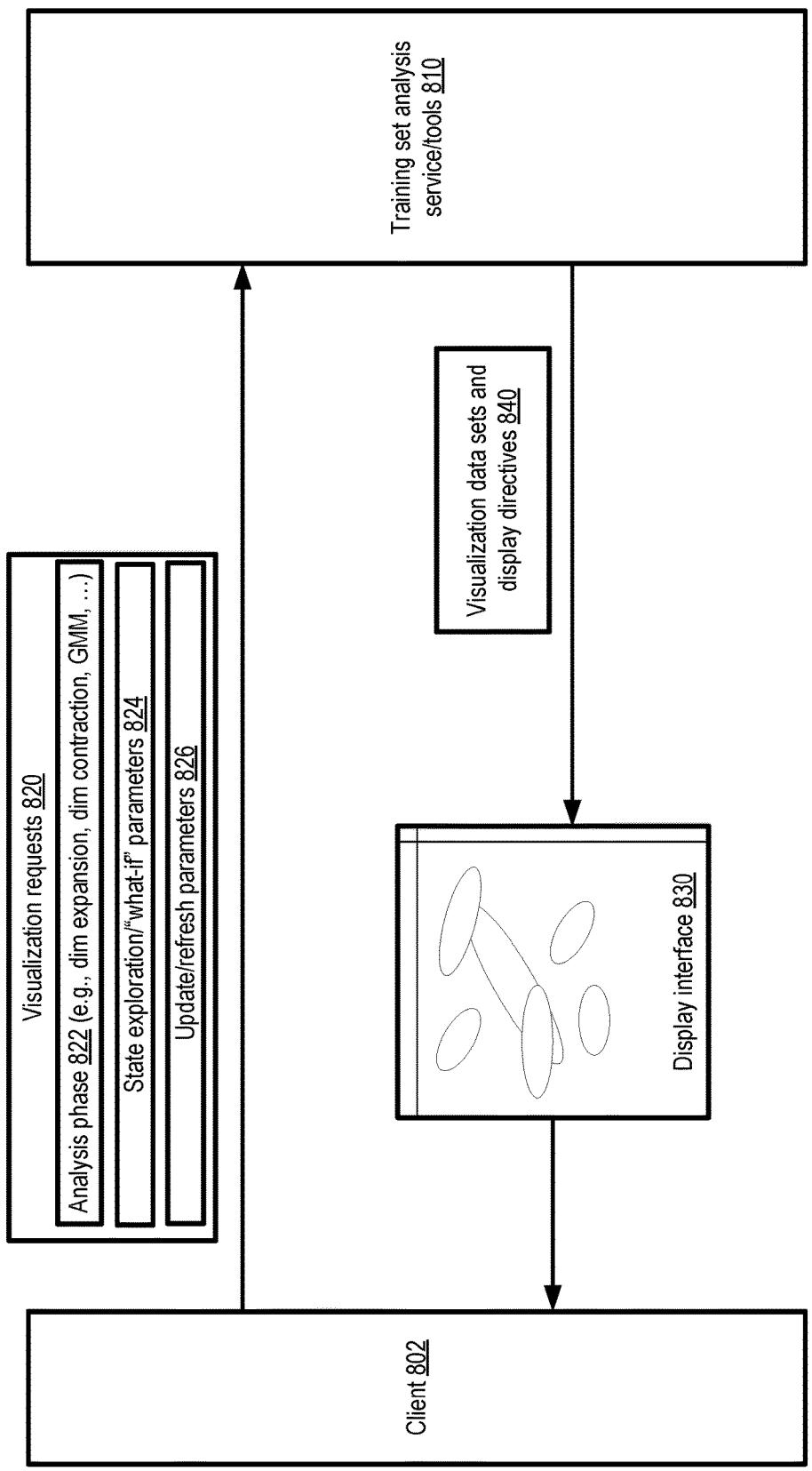
FIG. 8 illustrates aspects of example visualization-related programmatic interactions between a client and a training set analysis service, according to at least some embodiments.

FIG. 8 illustrates aspects of example visualization-related programmatic interactions between a client and a training set analysis service, according to at least some embodiments. As shown, a client 802 of a training set analysis service or tool 810 may submit visualization requests 820 in the depicted embodiment, e.g., via a programmatic interface implemented by the service or tool. A visualization request 820 may include one or more parameters such as an indication 822 of the analysis phase whose results are to be displayed in the depicted embodiment. In some embodiments, the request may include one or more other parameters, such as one or more state exploration or "what-if" parameters 824 and/or refresh/update parameters 826. The exploration or what-if parameters 824 may suggest one or more ways in which settings or model parameters for specified operations at the training set analysis service or tools 810 should be modified, and the specified operations re-run, to provide a visual representation of an impact of the changes to the settings/model parameters. For example, as discussed earlier in several phases random forest algorithms may be used during the analysis of training data, and the exploration parameters 824 may be used to request changes to the random forest parameters (such as the number of trees per forest, maximum tree depth and/or minimum leaf size) and a re-execution of the corresponding phase of the analysis in some embodiments. The refresh/update parameters 826 may be used in some embodiments to indicate how often a visualization should be dynamically updated. For example, in one embodiment, it may be the case that the results of the Gaussian mixture model phase of the analysis are displayed dynamically as they become available, and a refresh parameter may indicate that the display should be automatically updated once every t seconds as new data becomes available. In at least one embodiment, a visualization request 820 may indicate that respective results of Gaussian mixture models with respect to a proposed training data set and a corresponding test set may presented graphically together (e.g., in side-by-side windows/panels or in the same window/panel), e.g., so that a visual comparison of the distributions of the proposed training data and the test data is made possible.

In the depicted embodiment, in response to a visualization request 820, the training data analysis service or tool 810 may prepare the data needed to generate the requested visualization, e.g., by accessing the data from one or more artifact repositories used to store intermediate and/or final results of the analysis being performed. Visualization data sets 840 with accompanying display directives (e.g., instructions for laying out the data on a screen) may be transmitted to a client device with a display interface 830, where the data sets may be arranged graphically for viewing by the client.

High Level Application Programming Interface Examples

In some embodiments, a set of application programming interfaces (APIs) may be implemented to enable clients to interact with the training data analysis tool or service, e.g., to obtain visualizations as discussed above, to submit analysis requests for specified data sets, to obtain or set various meta-parameters of the analysis and so on. In one embodiment, in addition to or instead of APIs, other programmatic interfaces such as a web-based console, command-line tools, and/or one or more graphical user interfaces may be implemented for similar types of interactions.

A database or repository of a set of objects or artifacts may be maintained by the training data analysis service or tool in various embodiments, comprising persistent representations of various data structures, meta-parameters, model parameters, results and the like at various stages of the analysis. In at least some embodiments, the repository may be searchable by clients, e.g., using one or more APIs similar to the following:

1. handle=searchHandle(searchString, accessCredentials)

In API 1 shown above, the searchString parameter may indicate one or more search parameters to be used to obtain a pointer or handle to the artifact of interest, while the accessCredentials parameter may indicate the credentials (e.g., roles/capabilities/permissions) granted to the requesting client. In response to the invocation of the searchHandle API, a data set may be provided by the service in some embodiments, e.g., as a result of an invocation of an API similar to API 2 shown below.

2. handle=sendData(dataset, columns, ignore-column-list, column-types)

In API 2 the data set is assumed to comprise some number of rows or records, with each row comprising values of one or more columns (as indicated by the columns parameter and their associated data types column-types). The ignore-column-list parameter may be used to indicate that some of the columns are to be filtered out or ignored in some embodiments.

In some embodiments, visualization-related APIs such as the following may be implemented by the training data analysis tool:

3. visualizationObj=getVisualization(handle)
4. visualizationObj=updateVisualization(visualizationObj, parameterList)

API 3 may be used to obtain a data set associated with a handle (corresponding to some object or artifact) for visualization, while API 4 may be used to refresh or update the data set in various embodiments. In at least some embodiments, a plotting tool associated with or provided by the training data analysis service may accept visualization objects and save them to local files. The plotting tool may implement various features for highlighting or marking portions of a data set, and storing the information about the highlighted/marked portions as a visualizationConfiguration object which may be used for the actual display of the data. The plotting tool may be designed to display Gaussian mixture models (represented for example by GMMObjects as shown below in API 5). In addition, APIs may be used to set an ambiguous score range for a classifier (which can then be used to the within-ambiguity-threshold subset 528 of data points discussed in the context of FIG. 5) and/or to mark specified points as being ambiguous in some embodiments.

5. GMMObject=determineGMM(handle, numGMMs, cutOffParams)

In some embodiments, in API 5, the numGMMs parameter may indicate the total number of Gaussians to be included in the mixture, while cutOffParams may indicate for example the number of example data points within various subdivisions along the Gaussians' axes which are to be identified for inclusion in a training data set (e.g., within one standard deviation of the mean, within two standard deviations of the mean, etc.).

A number of parameters and meta-parameters of the analysis may be obtained (or set) using APIs in different embodiments, such as random forest parameters, the number of clusters to be generated in the K-means clustering phase and/or other phases, data subset sizes for various stages of the analysis, GMM objects, visualization objects, visualization configuration objects, and so on. In at least one embodiment, APIs similar to the following may be implemented to enable subsets of data sets to be obtained:

6. dataSet=getSubset(handle)
7. dataSet=getSubset(handle, classifier, ambiguousPoints)
8. dataSet=getPoints(classifier, ambiguousPoints)

It is noted that in various embodiments, APIs other than those discussed above may be used to support various types of client interactions with the training data analysis service or tool—the high-level APIs listed are not meant to be restrictive. In some embodiments, for example an API such as analyze TrainingData(dataset, metaparameterList) may be used to initiate a workflow of the kind illustrated in FIG. 2, with the input set of observations being indicated in the dataset parameter, and zero or more meta-parameters of the analysis being indicated in metaparameterList.

Provider Network Environment

Figure 9:
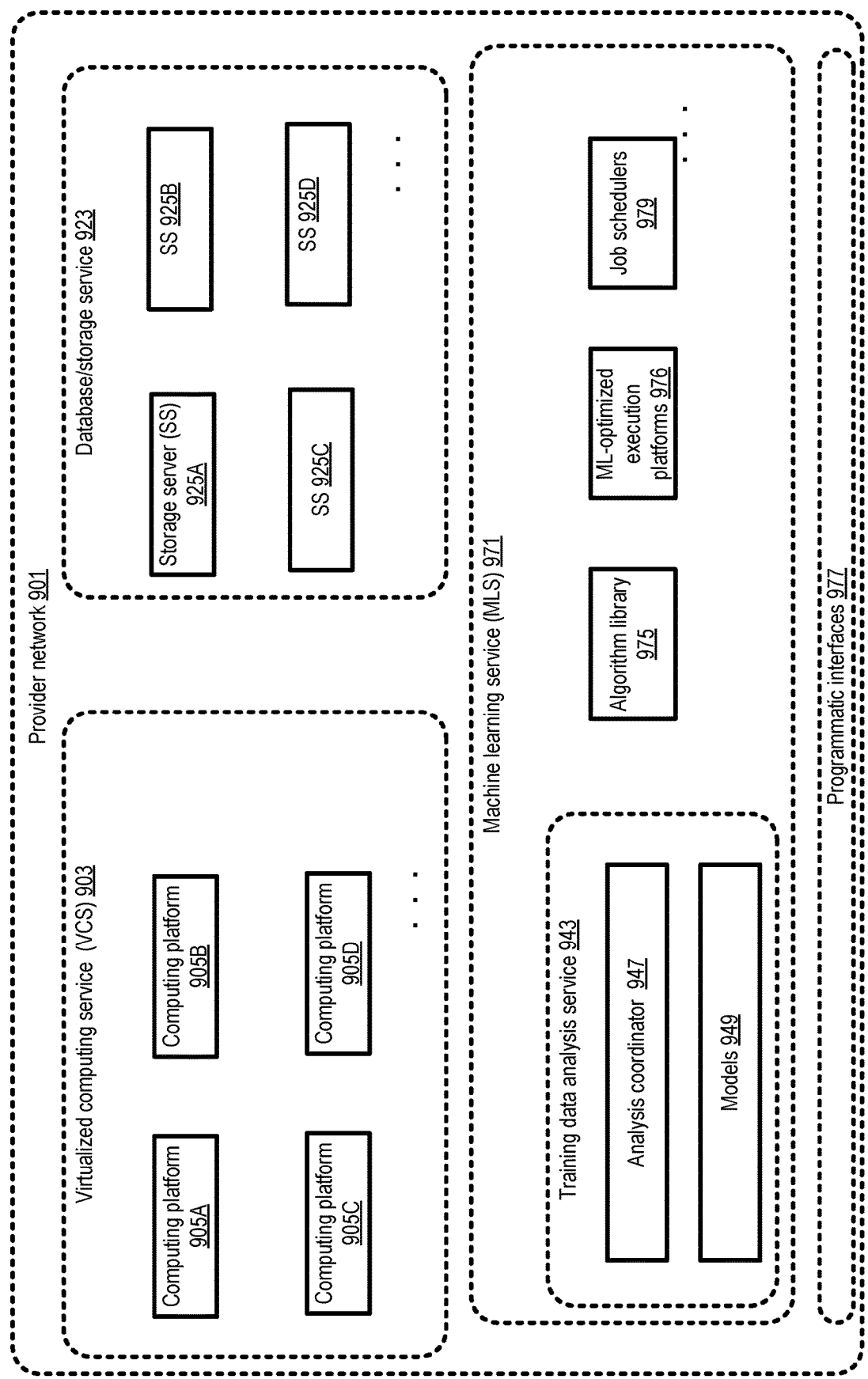
FIG. 9 illustrates a provider network environment at which a machine learning service may be implemented, according to at least some embodiments.

In some embodiments, the techniques discussed above for analyzing and improving training data may be implemented at a network-accessible machine learning service. FIG. 9 illustrates a provider network environment at which a machine learning service may be implemented, according to at least some embodiments. Networks set up by an entity such as a company or a public sector organization to provide one or more network-accessible services (such as various types of cloud-based computing, storage or analytics services) accessible via the Internet and/or other networks to a distributed set of clients may be termed provider networks in one or more embodiments. A provider network may sometimes be referred to as a "public cloud" environment. The resources of a provider network may in some cases be distributed across multiple data centers, which in turn may be distributed among numerous geographical regions (e.g., with each region corresponding to one or more cities, states or countries).

In the depicted embodiment, provider network 901 may comprise resources used to implement a plurality of services, including for example a virtual computing service 903, a database or storage service 923, a machine learning service 971. The machine learning service 971 may comprise a training data analysis service 943 in some embodiments; in other embodiments, the training data analysis service may be implemented as a separate service of the provider network. Components of a given service may utilize components of other services in the depicted embodiment—e.g., for some machine learning tasks, a component of the machine learning service 971 may utilize virtual machines implemented at computing platforms such as 905A-905D of the virtualized computing service. Input data, intermediate results, final results and/or other artifacts of various machine learning algorithms or models may be stored at storage servers 925 (e.g., 925A-925D) of the database or storage service 923 in some embodiments. Individual ones of the services shown in FIG. 9 may implement a respective set of programmatic interfaces 977 which can be used by external and/or internal clients (where the internal clients may comprise components of other services) in the depicted embodiment.

As shown, the training data analysis service 943 may comprise, among other components, one or more analysis coordinator 947 and a collection of models 949 in the depicted embodiment. The analysis coordinator 947 may, for example, invoke algorithms selected from the machine learning algorithm library 975 to train the various models required to implement workflows similar to those shown in FIG. 2 in the depicted embodiment. In some embodiments, requests to train machine learning models may be handled as batch jobs at the machine learning service, and a batch job scheduler 979 may orchestrate the allocation of resources for the jobs as well as dependencies among jobs. In at least one embodiment, a machine learning service 971 may have access to or include a set of execution platforms 976 that are optimized for machine learning tasks (e.g., platforms that have customized hardware such as GPU arrays and/or customized software stacks). Depending on the suitability of such platforms for training data analysis tasks and/or the types of classifiers for which the training data is being analyzed, one or more execution platforms 976 may be employed in the depicted embodiment.

In at least some embodiments, the training data analysis workflows discussed earlier may be accomplished using non-specialized computing platforms of the virtualized computing service. In various embodiments, the training and test/evaluation data used for various models may be stored at a database/storage service 923. As mentioned earlier, the techniques for training data analysis described above may be implemented without acquiring resources of network-accessible services such as those shown in FIG. 9 in at least some embodiments. For example, a standalone tool implemented at one or more computing devices which are not part of a network-accessible service may be used in some embodiments.

Methods for Training Data Analysis

Figure 10:
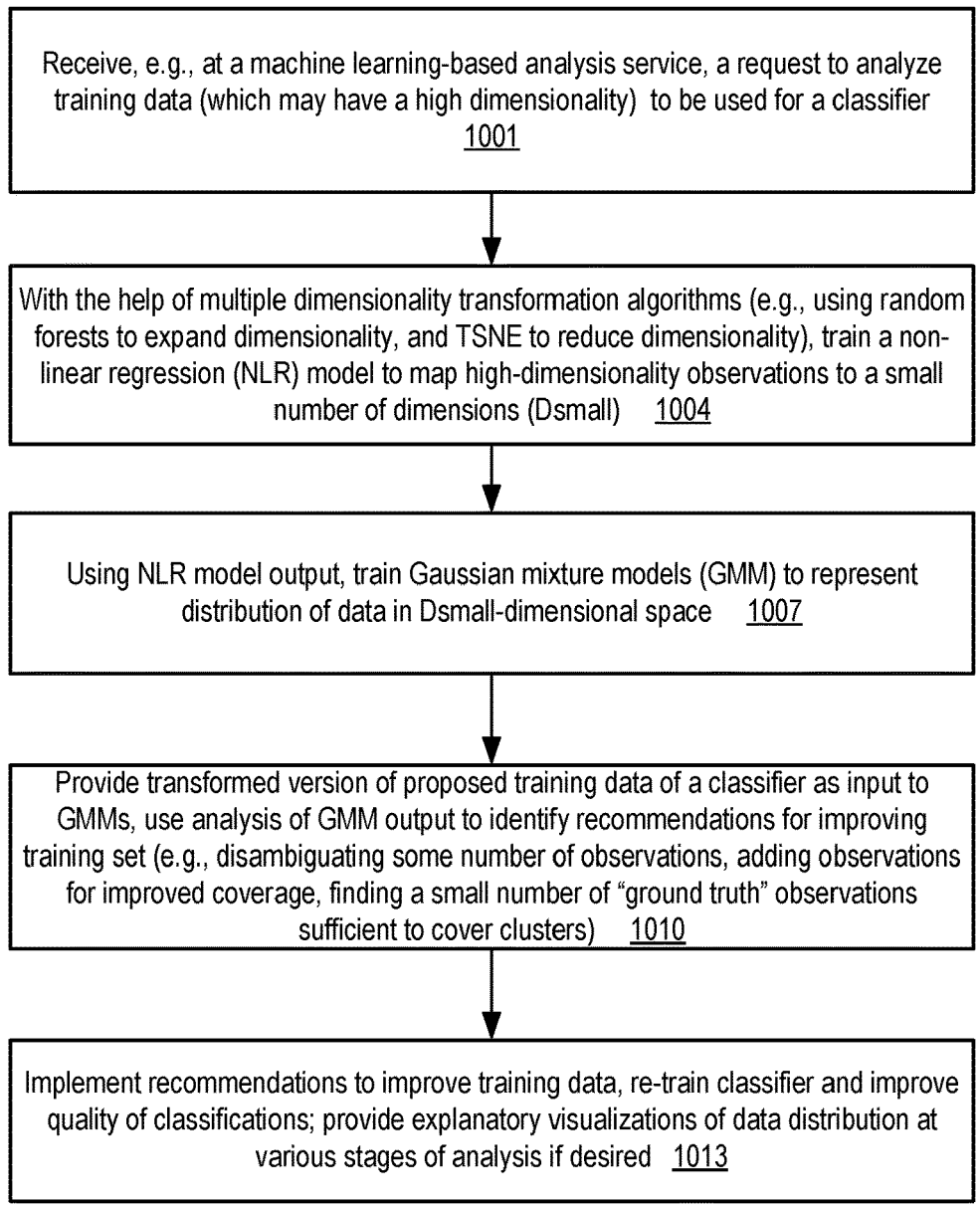
FIG. 10 is a flow diagram illustrating aspects of operations that may be performed to analyze training data sets used for machine learning models, according to at least some embodiments.

FIG. 10 is a flow diagram illustrating aspects of operations that may be performed to analyze training data sets used for machine learning models, according to at least some embodiments. As shown in element 1001, a request may be received, e.g., at a machine learning based analysis service or tool, to analyze a training set to be used for a classifier. The request may be received, for example, via a programmatic interface such as an API, a web-based console, a graphical user interface, or a command line tool in various embodiments, and may indicate the set of data which is to be analyzed, e.g., by providing a pointer or address of such data, or by providing the training data itself as a parameter. Individual observation records of the training set may comprise respective values for a high number of features or attributes in some embodiments, with potentially non-linear relationships between the attributes and the target or output variable. In some embodiments, the analysis request may include proposed or recommended settings for one or more meta-parameters of the analysis.

As indicated in element 1004, a multi-variate non-linear regression (NLR) model may be trained to map the input observations to a small number of dimensions Dsman in some embodiments, using a number of dimension transformation algorithms as part of the procedure used to train the NLR model. For example, in one embodiment, a first dimensionality expansion algorithm (e.g., using random forests and one-hot-encoding) may be applied to the training data, e.g., to obtain a clearer separation among the observation classes, and then a dimensionality contraction algorithm (e.g., TSNE) may be used to map the expanded-dimension records back to some small number of dimensions while retaining the proximity relationships among transformed observations exhibited in the expanded number of dimensions. In some embodiments, at least a portion of the training data set may be clustered (e.g., using a K-means clustering algorithm) before one or more of the dimensionality transformation operations are performed.

Using transformed records obtained as the output of the non-linear regression model, a Gaussian mixture model (GMM) may be trained in some embodiments (element 1007) to represent the distribution of the data in $D_{small}$ dimensions. A transformed version of a proposed training data of a classifier may be provided as input to the GMM (element 1010). The GMM output may be analyzed to identify one or more recommendations for improving the proposed training set (e.g., by disambiguating some number of observations, adding observations for improved coverage, finding a small number of "ground truth" observations sufficient to cover clusters identified in a test data set, and so on). In some embodiments, for example, a small number of points within a selected distance from the mean or centroid of an ellipsoid representation of a Gaussian distribution (e.g., within a small multiple of the standard deviation along an axis of the ellipsoid) may be identified for disambiguation. In one embodiment, the distribution in the GMM output of a proposed training data subset and a test data set may be compared, and some number of observations may be added to the proposed training data set if the comparison indicates that there are insufficient points in some clusters of the proposed training data set relative to the test data.

In various embodiments, the recommendations to improve the training data may be implemented, e.g., by adding observations with the desired characteristics to the proposed training data set in an automated manner (element 1013). The classifier may be retrained using the improved training data in an iterative manner to improve the quality of its classifications. Explanatory visualizations of data distribution at various stages of analysis, responses to exploratory queries which change parameters or steps of the analysis, and so on, may be provided via programmatic interfaces in some embodiments.

It is noted that in various embodiments, some of the operations shown in FIG. 10 (and/or other flow diagrams presented earlier) may be implemented in a different order than that shown in the figure, or may be performed in parallel rather than sequentially. Additionally, some of the operations shown in FIG. 10 or other flow diagrams may not be required in one or more implementations.

Evaluation Examples

In one embodiment, approaches similar to the following may be taken to verify that the quality of the classifications achieved is improved by implementing some of the types of training data set analysis steps discussed above. In the example provided below, an "active set" of observation records may be identified to replace a set of ambiguously-labeled observations for a binary classifier.

Assume that a training set (TrainSet) and a test set (TestSet) have been identified for a classifier. Assume further that a set of ambiguous observations AmbSet within TrainSet has been determined, e.g., based on binary classification scores that lie within some delta of 0.5 (e.g., between 0.45 and 0.55), where the classification score of 0.5 represents the boundary between the classes. Let Model(X) represent a classifier trained using data set X, Predict(X', Model(X)) represent the predictions made on data X' by Model(X), and Metrics(X', Model(X)) represent some set of metrics regarding the quality of the predictions Predict(X' Model(X)). A number of different metrics may be used singly or in combination for the evaluation of the training set improvement technique in different embodiments, such as accuracy, precision, recall, area under the receiver operating characteristic (ROC) curve (which may also be referred to as AUC), and so on. A higher value of the metric (or combination of metrics) being considered is assumed to be superior to a lower value.

Let a random subset of AmbSet be denoted as RandSet, and let an active subset of AmbSet (e.g., identified using a workflow similar to that shown in FIG. 2) be denoted as ActiveSet. Given these notations, in at least some embodiments the methodology being applied may be assumed to be successful in improving the quality of the training data, given the test data TestSet, if the following inequalities hold: Inequalities 1:

Metrics(TestSet,TrainSet−AmbSet)<Metrics(TestSet, TrainSet−AmbSet+RandSet)<Metrics(TestSet, TrainSet−AmbSet+ActiveSet)

As per Inequality 1, the quality of the classifications, when the ambiguous data is replaced in the training set by the active set of data identified using the analysis, is superior to the quality when the ambiguous data is replaced by a random subset (or the quality when the ambiguous data is simply removed).

In a second approach towards improving classification quality using an active set of observations which may be employed in some embodiments, model instability may be considered as a quality metric. Model instability may be manifested, for example, when a binary classification label for a given observation record "flickers" or changes as minor changes are made to the model during training. Such flickering or flipping may be reduced in some embodiments by adding more training data identified using a workflow similar to that shown in FIG. 2, with the following approach being used for evaluation.

Let the notation $\text{Flips}^{-Ambset}$ denote that differences (flips) in labels between using the training set as a whole, and removing the ambiguous set prior to training the model. Thus, $$\text{Flips}^{-Ambset} = \text{Predict}(\text{TestSet},\text{Model}(\text{TrainSet})) \sim \text{Predict}(\text{TestSet},\text{Model}(\text{TrainSet}-\text{AmbSet}))$$

where the "~" indicates difference. Further, let $\text{Flips}^{+Rand}$ denote the differences in labels when a random subset of the ambiguous set is added back in, and $\text{Flips}^{+Active}$ denote the differences in labels when the active subset of the ambiguous set (identified using a workflow similar to that shown in FIG. 2) is added back in. Thus, $$\text{Flips}^{+Rand} = \text{Predict}(\text{TestSet},\text{Model}(\text{TrainSet})) \sim \text{Predict}(\text{TestSet},\text{Model}(\text{TrainSet}-\text{AmbSet}+\text{RandSet}))$$

and $$\text{Flips}^{+Active} = \text{Predict}(\text{TestSet},\text{Model}(\text{TrainSet})) \sim \text{Predict}(\text{TestSet},\text{Model}(\text{TrainSet}-\text{AmbSet}+\text{ActiveSet}))$$

The methodology for improving the training set may be said to be successful with regard to model instability of the kind discussed above if the following inequalities hold in at least some embodiments:

$$\text{Flips}^{-Ambset} > \text{Flips}^{+Rand} > \text{Flips}^{+Active} \qquad \text{Inequalities 2}$$

As per inequalities 2, replacing the ambiguous data of a training data set by an active subset reduces the instability more than if a random subset were used for the replacement (which in turn reduces the instability more than if no replacement were made). Other approaches towards evaluation may be taken in other embodiments.

Use Cases

The techniques described above, of analyzing the distribution of high-dimensional observation data that may have non-linear relationships with target/output features with the goal of improving training sets for classifiers and/or other machine learning models may be useful in a variety of scenarios. For many machine learning applications including classification models, very large data sets (e.g., millions or billions of observations) may be used for training and testing the models. Using the raw data itself, it may be very hard to visualize or understand the separation between classes of the observations. It may also be hard to judge whether the distribution of observations of a given proposed training data set provides enough examples for all the clusters which may be present in data for which the trained model is deployed in a production environment. By using the dimension transformation-based techniques and associated visualization capabilities discussed, it may become easier to discern the differences in distributions between proposed training data and test data. By automatically identifying a small subset of ambiguously-labeled points whose labels can be verified/disambiguated, or adding a small number of observations to a proposed training set to improve coverage, significant improvements in the quality of the classification results may be obtained, and the overall resource usage required for training classifiers may be reduced.

Illustrative Computer System

Figure 11:
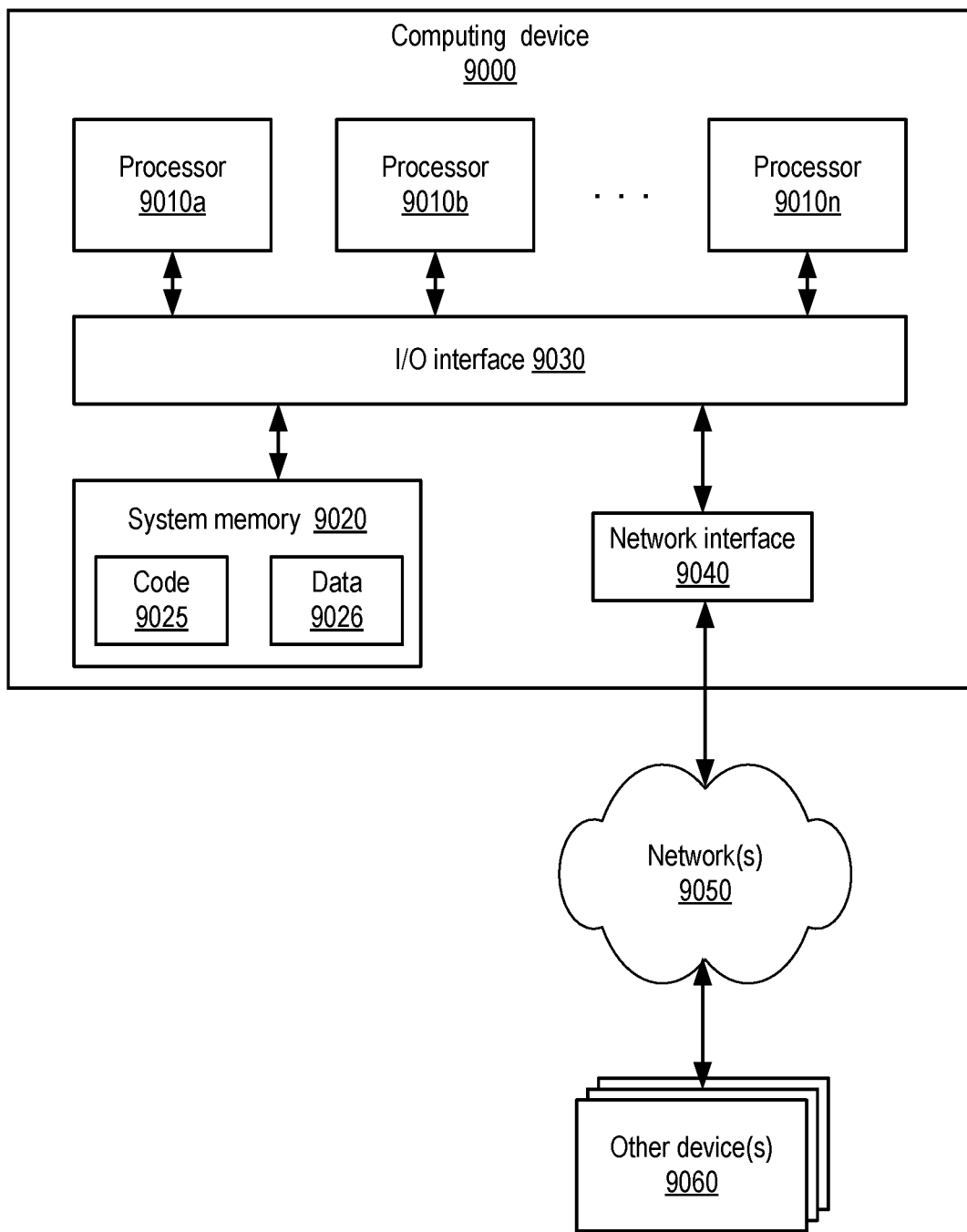
FIG. 11 is a block diagram illustrating an example computing device that may be used in at least some embodiments.

In at least some embodiments, a server that implements a portion or all of one or more of the technologies described herein, including the training and execution of machine learning models for analysis/improvement of training data used for classification, as well as the classifiers themselves, may include a general-purpose computer system that includes or is configured to access one or more computer-accessible media. FIG. 11 illustrates such a general-purpose computing device 9000. In the illustrated embodiment, computing device 9000 includes one or more processors 9010 coupled to a system memory 9020 (which may comprise both non-volatile and volatile memory modules) via an input/output (I/O) interface 9030. Computing device 9000 further includes a network interface 9040 coupled to I/O interface 9030.

In various embodiments, computing device 9000 may be a uniprocessor system including one processor 9010, or a multiprocessor system including several processors 9010 (e.g., two, four, eight, or another suitable number). Processors 9010 may be any suitable processors capable of executing instructions. For example, in various embodiments, processors 9010 may be general-purpose or embedded processors implementing any of a variety of instruction set architectures (ISAs), such as the x86, PowerPC, SPARC, or MIPS ISAs, or any other suitable ISA. In multiprocessor systems, each of processors 9010 may commonly, but not necessarily, implement the same ISA. In some implementations, graphics processing units (GPUs) may be used instead of, or in addition to, conventional processors.

System memory 9020 may be configured to store instructions and data accessible by processor(s) 9010. In at least some embodiments, the system memory 9020 may comprise both volatile and non-volatile portions; in other embodiments, only volatile memory may be used. In various embodiments, the volatile portion of system memory 9020 may be implemented using any suitable memory technology, such as static random access memory (SRAM), synchronous dynamic RAM or any other type of memory. For the non-volatile portion of system memory (which may comprise one or more NVDIMMs, for example), in some embodiments flash-based memory devices, including NAND-flash devices, may be used. In at least some embodiments, the non-volatile portion of the system memory may include a power source, such as a supercapacitor or other power storage device (e.g., a battery). In various embodiments, memristor based resistive random access memory (ReRAM), three-dimensional NAND technologies, Ferroelectric RAM, magnetoresistive RAM (MRAM), or any of various types of phase change memory (PCM) may be used at least for the non-volatile portion of system memory. In the illustrated embodiment, program instructions and data implementing one or more desired functions, such as those methods, techniques, and data described above, are shown stored within system memory 9020 as code 9025 and data 9026.

In one embodiment, I/O interface 9030 may be configured to coordinate I/O traffic between processor 9010, system memory 9020, and any peripheral devices in the device, including network interface 9040 or other peripheral interfaces such as various types of persistent and/or volatile storage devices. In some embodiments, I/O interface 9030 may perform any necessary protocol, timing or other data transformations to convert data signals from one component (e.g., system memory 9020) into a format suitable for use by another component (e.g., processor 9010). In some embodiments, I/O interface 9030 may include support for devices attached through various types of peripheral buses, such as a variant of the Peripheral Component Interconnect (PCI) bus standard or the Universal Serial Bus (USB) standard, for example. In some embodiments, the function of I/O interface 9030 may be split into two or more separate components, such as a north bridge and a south bridge, for example. Also, in some embodiments some or all of the functionality of I/O interface 9030, such as an interface to system memory 9020, may be incorporated directly into processor 9010.

Network interface 9040 may be configured to allow data to be exchanged between computing device 9000 and other devices 9060 attached to a network or networks 9050, such as other computer systems or devices as illustrated in FIG. 1 through FIG. 10, for example. In various embodiments, network interface 9040 may support communication via any suitable wired or wireless general data networks, such as types of Ethernet network, for example. Additionally, network interface 9040 may support communication via telecommunications/telephony networks such as analog voice networks or digital fiber communications networks, via storage area networks such as Fibre Channel SANs, or via any other suitable type of network and/or protocol.

In some embodiments, system memory 9020 may be one embodiment of a computer-accessible medium configured to store program instructions and data as described above for FIG. 1 through FIG. 10 for implementing embodiments of the corresponding methods and apparatus. However, in other embodiments, program instructions and/or data may be received, sent or stored upon different types of computer-accessible media. Generally speaking, a computer-accessible medium may include non-transitory storage media or memory media such as magnetic or optical media, e.g., disk or DVD/CD coupled to computing device 9000 via I/O interface 9030. A non-transitory computer-accessible storage medium may also include any volatile or non-volatile media such as RAM (e.g. SDRAM, DDR SDRAM, RDRAM, SRAM, etc.), ROM, etc., that may be included in some embodiments of computing device 9000 as system memory 9020 or another type of memory. Further, a computer-accessible medium may include transmission media or signals such as electrical, electromagnetic, or digital signals, conveyed via a communication medium such as a network and/or a wireless link, such as may be implemented via network interface 9040. Portions or all of multiple computing devices such as that illustrated in FIG. 11 may be used to implement the described functionality in various embodiments; for example, software components running on a variety of different devices and servers may collaborate to provide the functionality. In some embodiments, portions of the described functionality may be implemented using storage devices, network devices, or special-purpose computer systems, in addition to or instead of being implemented using general-purpose computer systems. The term "computing device", as used herein, refers to at least all these types of devices, and is not limited to these types of devices.

CONCLUSION

Various embodiments may further include receiving, sending or storing instructions and/or data implemented in accordance with the foregoing description upon a computer-accessible medium. Generally speaking, a computer-accessible medium may include storage media or memory media such as magnetic or optical media, e.g., disk or DVD/CD-ROM, volatile or non-volatile media such as RAM (e.g. SDRAM, DDR, RDRAM, SRAM, etc.), ROM, etc., as well as transmission media or signals such as electrical, electromagnetic, or digital signals, conveyed via a communication medium such as network and/or a wireless link.

The various methods as illustrated in the Figures and described herein represent exemplary embodiments of methods. The methods may be implemented in software, hardware, or a combination thereof. The order of method may be changed, and various elements may be added, reordered, combined, omitted, modified, etc.

Various modifications and changes may be made as would be obvious to a person skilled in the art having the benefit of this disclosure. It is intended to embrace all such modifications and changes and, accordingly, the above description to be regarded in an illustrative rather than a restrictive sense.

What is claimed is:

1. A system, comprising:
one or more computing devices of an artificial intelligence service for analysis of training data sets for machine learning models;
wherein the one or more computing devices are configured to:
obtain an indication of a first data set comprising a plurality of observation records, wherein individual ones of the observation records comprise a first feature set and have a baseline dimensionality;
apply a dimensionality expansion algorithm to at least a portion of the first data set to obtain a second data set, wherein individual ones of records of the second data set have a second dimensionality, wherein the second dimensionality is higher than the baseline dimensionality;
utilize a dimensionality contraction algorithm to map the second data set to a third data set, wherein individual ones of transformed records of the third data set have a third dimensionality, wherein the third dimensionality is lower than the second dimensionality, wherein at least some proximity relationships among a set of records of the second data set are preserved among a set of transformed records of the third data set after mapping of the second data set to the third data set;
train, using the first data set and the third data set, a multivariate regression model to map observation records comprising the first feature set into transformed records with the third dimensionality;
train, using a set of transformed records obtained as output from the multivariate regression model, a Gaussian mixture model of distributions of observation records within a space with the third dimensionality;
determine, with respect to one or more Gaussian distributions obtained from the Gaussian mixture model, a disambiguation count indicating, within a proposed training set of a classifier, a target number of observation records for which label disambiguation is recommended; and
provide an indication of at least the disambiguation count to a destination.

2. The system as recited in claim 1, wherein the one or more computing devices are configured to:
obtain a first result of the Gaussian mixture model with respect to the proposed training set;
obtain a second result of the Gaussian mixture model with respect to a post-training data set to be classified using the classifier; and
determine, based at least in part on a result of comparison of the first result with the second result, one or more recommended modifications of the proposed training set.

3. The system as recited in claim 2, wherein a particular recommended modification of the one or more recommended modifications comprises a recommendation to add one or more observation records.

4. The system as recited in claim 1, wherein the one or more computing devices are configured to:
determine that a visualization request has been received via a programmatic interface of the artificial intelligence service, wherein the visualization request indicates at least an analysis phase whose results are to be displayed, wherein the analysis phase comprises one or more of (a) a dimensionality expansion phase, (b) a dimensionality contraction phase, (c) a Gaussian mixture analysis phase; and
transmit, to a destination device, (a) a response data set representing values of one or more dimensions of output records generated by the analysis phase, and (b) a directive to display at least a portion of the response data set.

5. The system as recited in claim 1, wherein the one or more computing devices are configured to:
determine that a request to analyze the proposed training set for the classifier has been received via a programmatic interface of the artificial intelligence service.

6. A method, comprising:
performing, by one or more computing devices:
training a regression model to map an observation record of a first dimensionality into a transformed record of a second dimensionality, wherein said training comprises utilizing results of one or more dimensionality modification operations on one or more observation records;
training, using a set of transformed records obtained using the regression model, a Gaussian mixture model of distributions of observation records within a space with the second dimensionality;
determining, with respect to a first Gaussian distribution obtained from the Gaussian mixture model, a first disambiguation count indicating a target number of observation records within a proposed training set of a classifier to be recommended for label disambiguation; and
storing an indication of the first disambiguation count.

7. The method as recited in claim 6, further comprises performing, by the one or more computing devices:
generating a first training set for the regression model, wherein said generating the first training set for the regression model comprises:
applying a dimensionality expansion algorithm to a particular observation record to obtain a first intermediate record with a third dimensionality, wherein the third dimensionality is higher than the first dimensionality; and
applying a dimensionality contraction algorithm to the first intermediary record to obtain a second intermediate record with the second dimensionality, wherein the second dimensionality is lower than the third dimensionality.

8. The method as recited in claim 7, wherein the dimensionality expansion algorithm comprises a use of one or more of: a random forest algorithm or a one-hot encoding algorithm.

9. The method as recited in claim 7, wherein the dimensionality contraction algorithm comprises one or more of: (a) a Principal Component Analysis (PCA) algorithm, (b) a multi-dimensional scaling (MDS) algorithm (c) a t-distributed stochastic neighbor embedding (TSNE) algorithm, or (d) a matrix factorization algorithm.

10. The method as recited in claim 7, wherein said generating the first training data set for the regression model comprises:
   implementing a clustering algorithm on a plurality of observation records; and
   selecting, based at least in part on a result of said clustering algorithm, the particular observation record for inclusion in the first training data set.

11. The method as recited in claim 6, wherein the regression model comprises a multi-variate nonlinear regression model.

12. The method as recited in claim 6, wherein the regression model comprises a random forest model.

13. The method as recited in claim 6, further comprising performing, by the one or more computing devices:
   obtaining a first result of the Gaussian mixture model with respect to the proposed training set;
   obtaining a second result of the Gaussian mixture model with respect to a post-training data set;
   transmitting, to one or more target devices, a representation of the first result, a representation of the second result, and a directive to display the first and second result sets.

14. The method as recited in claim 6, wherein said training the first regression model is responsive to:
   determining that a request to analyze a training set for the classifier has been received via a programmatic interface of a network-accessible service, wherein the request indicates a data set comprising a plurality of observation records with the first dimensionality.

15. The method as recited in claim 6, further comprising:
   partitioning an axis corresponding to an ellipsoid representation of the first Gaussian distribution, wherein said partitioning is based at least in part on a variation-related metric of the first Gaussian distribution; and
   performing one or more iterations of an optimization algorithm, wherein a particular iteration comprises obtaining a result set from the classifier using a second proposed training set which comprises one or more observations mapped to a particular group of partitions of the axis.

16. A non-transitory computer-accessible storage medium storing program instructions that when executed on one or more processors cause the one or more processors to:
   generate a regression model to map an observation record of a first dimensionality into a transformed record of a second dimensionality;
   train, using a set of transformed records obtained using the regression model, a Gaussian mixture model of distributions of observation records within a space with the second dimensionality; and
   store an indication of one or more recommended modifications of a first proposed training set of a classifier, including a first recommended modification determined at least in part using a first Gaussian distribution obtained from the Gaussian mixture model, wherein the first recommended modification indicates a number of observation records within the first proposed training set of the classifier whose labels are recommended to be disambiguated.

17. The non-transitory computer-accessible storage medium as recited in claim 16, wherein the first recommended modification includes a recommendation to disambiguate a respective label associated with one or more observation records of the first proposed training set.

18. The non-transitory computer-accessible storage medium as recited in claim 16, wherein the first recommended modification includes a recommendation to add one or more observation records to the first proposed training set.

19. The non-transitory computer-accessible storage medium as recited in claim 16, wherein the instructions when executed on the one or more processors cause the one or more processors to:
   determine that a request to generate a set of one or more models to enhance training sets for classifiers has been received via a programmatic interface of a network-accessible service, wherein one or more models of the regression model and the Gaussian mixture model are trained in response to the request.

20. The non-transitory computer-accessible storage medium as recited in claim 16, wherein the instructions when executed on the one or more processors cause the one or more processors to:
   identify, using one or more classification score thresholds, a candidate set of observation records of the proposed training set to be evaluated for disambiguation;
   provide, as input to the Gaussian mixture model, the candidate set of observation records to obtain the first Gaussian distribution.

* * * * *